United States Patent [19]

Baker, Jr.

[11] Patent Number: 4,679,572
[45] Date of Patent: Jul. 14, 1987

[54] LOW THRESHOLD CARDIAC PACING ELECTRODES

[75] Inventor: Ross G. Baker, Jr., Houston, Tex.

[73] Assignee: Intermedics, Inc., Angleton, Tex.

[21] Appl. No.: 838,607

[22] Filed: Mar. 11, 1986

[51] Int. Cl.[4] ............................................. A61N 1/05
[52] U.S. Cl. ................................... 128/786; 128/785; 128/419 P
[58] Field of Search .............................. 128/784–786, 128/419 P, 642

[56] References Cited

U.S. PATENT DOCUMENTS

| | | | |
|---|---|---|---|
| 3,735,766 | 5/1973 | Bowers et al. | 128/419 P |
| 4,407,302 | 10/1983 | Hirshom et al. | 128/419 P |
| 4,440,178 | 4/1984 | Bussard et al. | 128/419 P |
| 4,502,492 | 3/1985 | Bornzin | 128/785 |
| 4,573,481 | 3/1986 | Bullare | 128/784 |

OTHER PUBLICATIONS

Robblee et al, "Activated Ir: An Electrode . . . ", J. Electrochem Soc. pp. 731–733, vol. 130, No. 3, Mar. 1983.

Primary Examiner—Lee S. Cohen
Attorney, Agent, or Firm—Leitner, Greene & Christensen

[57] ABSTRACT

An electrode for use in cardiac pacemaking has a conductive tip portion including a substrate composed of a material conventionally employed for pacing electrodes, and a layer of film of iridium oxide overlying the surface of the substrate. The tip portion may be provided with recesses to which the iridium oxide surface layer may be confined. An iridium oxide layer may be formed on both the cathode and the anode for efficient transduction at the electrode-electroyte interface in the environment of the pacemaker patient's body.

11 Claims, 7 Drawing Figures

FIG.3
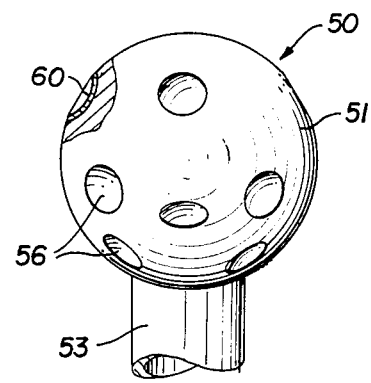
FIG.4
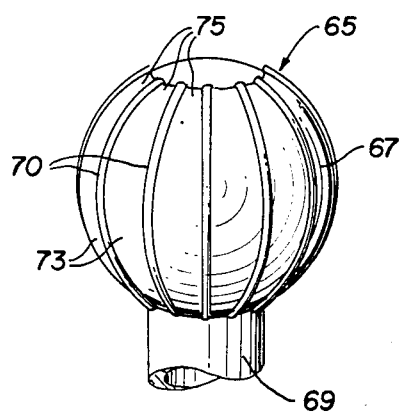
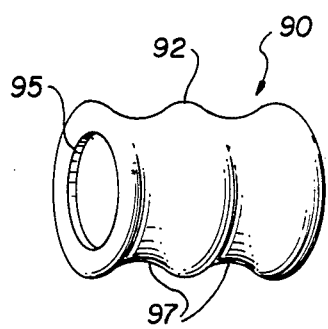
FIG.7
FIG.5
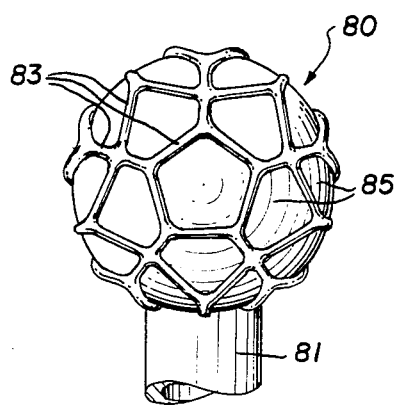
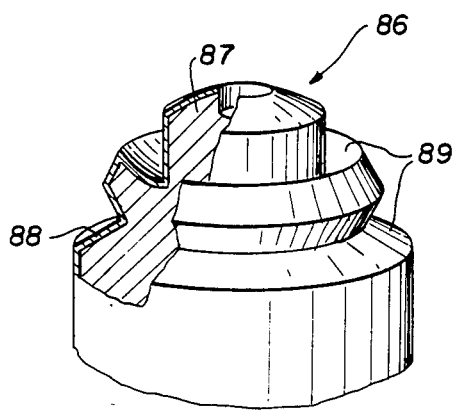
FIG.6

LOW THRESHOLD CARDIAC PACING ELECTRODES

BACKGROUND OF THE INVENTION

1. Field of the Invention

The present invention relates generally to artificial cardiac pacing, and more particularly to improved pacing electrodes for stimulating or sensing electrical activity of the heart, and to pacing lead assemblies incorporating such electrodes.

2. Prior Art

It is well known that the sinoatrial (S-A) node of the normal mammalian heart acts as the natural pacemaker by which rhythmic electrical excitation is developed and propagated to the atria. In response, the atrial chambers contract, pumping blood into the ventricles. The excitation is propagated the atrioventricular (A-V) node, which imposes a delay, and then via the conduction system consisting of the bundle of His and Purkinge fibers to the ventricular muscle, causing contraction and the pumping of blood from the ventricles. Disruption of this natural pacing/propagation system occurs as a result of aging and disease.

Where normal rate or rhythm is not spontaneously maintained in the heart beat of a human patient, the condition is corrected typically by utilizing an implantable cardiac pacemaker selected according to the particular deficiency of the patient. In its simplest form, the cardiac pacemaker consists of a pulse generator powered by a self-contained battery pack; a lead assembly including an electrode adapted to be positioned in stimulating relationship to excitable myocardial tissue either externally (an epicardial electrode) or internally (an endocardial electrode) of the heart, and an insulated electrically conductive lead interconnecting the pulse generator and the tissue-stimulating electrode to deliver the electrical stimuli to the tissue; and a second electrode connected to a reference potential, by which the electrical circuit is completed via body tissue and fluids. The entire lead assembly is often referred to simply as the lead, and the terminology "lead" and "electrode" are somtimes used interchangeably, albeit inaccurately.

For present purposes, the cardiac tissue-stimulating electrode utilized in the delivery of the pacing stimuli will sometimes be referred to herein as the stimulating cathodic electrode, or simply the cathode, and the other electrode will sometimes be referred to as the anodic electrode, or simply the anode. In fact, however, the coupling may be such that each electrode acts to a certain extent, at different times, as a cathode and an anode. In any event it is well known that activity takes place at each electrode in the delivery of the pacing stimuli.

The customary lead choice for the implantable cardiac pacemaker is an endocardial lead (or leads), because it is readily inserted pervenously to introduce the stimulating electrode into the chamber to be paced. In contrast, an epicardial lead requires thoracic surgery to affix the electrode to the heart. In either case, various means are employed to assure maintenance of positioning of the electrode relative to the excitable heart tissue. For epicardial leads, active fixation such as sutures or a sutureless screw-in electrode is employed. Endocardial leads may utilize active fixation such as a corkscrew, or passive fixation, which is less invasive, in the form of flexible barbs or hooks.

The implanted cardiac pacemaker may utilize a unipolar or bipolar lead system, depending on the preference of the physician and the needs of the patient. With unipolar stimulation, the anode is located remote from the heart, and typically comprises the metal case (or a portion thereof) that houses the batteries, pulse generator and other electronic circuitry of the pacemaker. For bipolar stimulation, the two electrodes are in relatively close proximity to one another, typically with the cathode at the electrode tip for contact with heart tissue, and the anode spaced slightly back from the tip as a ring or sleeve electrode.

In operation, output pulses from the pulse generator are delivered via the lead for electrical stimulation of the excitable myocardial tissue at or in the immediate vicinity of the site of the cathode, to produce the desired rhythmic contractions of the affected chamber. As is well known, stimulation is attributable to current density, and hence small area electrodes will suffice inasmuch as the current required to produce a given current density decreases in direct proportion to the active area of the electrode. Small area electrodes (cathodes) therefore serve to prolong battery life, resulting in a lengthening of the interval between required pacemaker replacements.

In essence, stimulation requires that an electric field of sufficient field strength and current density be impressed on the excitable tissue in the vicinity of the cathode contact site to initiate contraction. The minimum electrical impulse necessary to produce that effect is referred to as the stimulation threshold. The greater the efficiency of the cathode in impressing the electric field on the tissue, the smaller is the amplitude and/or duration of the pulse required to exceed the threshold. Accordingly, highly efficient, low threshold electrodes conserve energy and prolong battery life. Some authorities have theorized that because greater electrode efficiency lowers the energy required for stimulation, it is a factor in reducing injury to tissue at the stimulation site.

The chronic stimulation threshold for a given patient is typically on the order of two to three times greater than the acute threshold observed at the time of implantation and within the first few days thereafter. The increase in threshold is attributed to fibrotic growth; that is, the formation of a layer of non-excitable tissue about the electrode tip at the stimulation site. This fibrotic layer creates a virtual electrode surface area which is considerably greater than the actual surface area of the electrode, and consequently raises the stimulation threshold. Interestingly, the increase of chronic threshold over acute threshold is proportionately greater (to a limit) as electrode area is decreased, presumably because the ratio of virtual to actual surface area is higher for small area electrodes. Many authorities have speculated that the particular composition of the electrode may contribute to or retard fibrotic growth.

Cardiac pacing may be achieved with anodal, rather than cathodal stimulation, but the threshold for the former is higher than that attained with the latter. The reasons for this relate to the polarizing force of the stimulating electric field on ions at the surface of membranes of excitable myocardial cells subjected to the field. Suffice it to note that the highest current density and current flow exist at the side of each affected cell closest to the electrode. A cathodal pulse is depolarizing, or stimulating. In the case of anodal stimulation, however, the effect is hyperpolarizing, or nonstimulating. Reduction of transmembrane potential occurs on the side of each affected cell furthest from the anode, at a point of relatively lower field intensity, which is precisely opposite to the action that occurs with cathodal stimulation. Hence, the threshold for anodal stimulation is higher.

Numerous types of cardiac pacing electrodes have heretofore been developed with these and other factors in mind, utilizing various configurations and materials asserted to promote lower stimulation thresholds and improved electrical efficiencies.

SUMMARY OF THE INVENTION

I have found that by using an iridium oxide layer overlying the surface of the stimulating cathode of a cardiac pacemaker, a relatively large reduction in the threshold of stimulation is obtained, in comparison with the same electrode without such coating. I postulate that a corollary to the lower threshold will be a lessening of injury to tissue at the stimulation site. Moreover, iridium oxide appears to possess greater physical integrity and superior charge transfer capability per unit area than materials heretofore commonly employed for pacing electrodes, including specialized coatings such as platinum black.

Previously, it had been found and reported that iridium oxide films exhibit electrochromic behavoir, which led to the use of iridium oxide electrodes in electrochromic displays. Attention is invited, for example, to an article by Dautremont-Smith et al. entitled "Electrochromic Cells with Iridium Oxide Display Electrodes" appearing in *Solid State Ionics* 2 (1981) at pp. 13–18. Such iridium oxide films were produced by cyclic anodic growth on an iridium substrate, or by complete anodization of thin iridium films. A film prepared by anodizing techniques is designated by the acronym AIROF for anodic iridium oxide film. More recently, iridium oxide films have been produced by direct deposition on selected substrates through reactive sputtering from an iridium target. That type of iridium oxide films is referred to as a SIROFs, for sputter iridium oxide film.

Other investigators have reported the use of iridium oxide electrodes in medical applications, such as for use in measuring tissue impedances (see Gielen et al., "Comparison of electrode impedances of Pt, PtIr (10% Ir) and Ir-AIROF electrodes used in electrophysiological experiments", *Medical and Biological Engineering & Computing* (January 1982), pp. 77–83); for use in measuring acidity in the upper gastro-intestinal tract (see Papeschi et al., "The iridium/iridium oxide electrode for in vivo measurement of oesophagael and gastric pH", *Journal of Medical Engineering and Technology*, Vol. 8, No. 5 (Septemper–October 1984) pp. 221–223); and for use in measuring acidity changes in the blood (see Papeschi et al., "An iridium/iridium oxide electrode for in vivo monitoring of blood pH changes", *Journal of Medical Engineering and Technology*, Vol. 5, No. 2 (March 1981), pp. 86–88, and Cammilli et al., "Preliminary Experience with the pH-triggered Pacemaker", *PACE*, Vol. 1 (October–December 1978), pp. 448–457).

In the Cammilli et al. publication referenced above, the authors discuss the use of an iridium oxide electrode to sense blood pH in the right atrium. In particular, they reported having found the electrode useful for continuous in vivo detection of variations of mixed venous blood pH. According to the article, a rapid decrease of blood pH was utilized as a measure of variation of the patient's metabolic rate and employed to produce an appropriate variation in the stimulation rate of a pacemaker. Slow decrease of blood pH or any shift toward alkalinity produced no rate variation, and persistent acidosis resulted in a gradual return of the pacing rate to a pre-established baseline, according to the investigators.

So far as I am aware, no one has heretofore taught or suggested using an iridium oxide electrode for stimulating or sensing electrical activity of the heart. Indeed, in the medical applications of iridium oxide electrodes previously reported, the investigators would certainly have deemed any stray electrical signals as interfering with and undesirable to the purpose for which the electrodes were being used.

Although iridium oxide electrodes have been used more recently in electrophysiological experiments, such as for neuroelectrical experimentation with brain activity in small animals, the proposal for such use was attributable to an absolute requirement for extremely fine electrode wires, with active surface areas on the order of 20 square microns. It had been found that even platinum electrodes of such tiny size disintegrated on the passage therethrough of relatively low levels of current. It was found that an iridium oxide coating was capable of withstanding the necessary current without significant deterioration. In contrast to the relatively tiny surface areas of concern in these physiological experiments, electrodes for the stimulation of excitable heart tissue in artificial cardiac pacing, or for the detection of cardiac electrical activity, require comparatively greater surface areas.

My invention recognizes the extraordinary capability of iridium oxide to perform as a charge flow transducer between media exhibiting different charge flow mechanisms. Thus, despite the relatively inferior characteristic of iridium oxide as an electrical conductor compared to conventional pacing electrode materials, I have found that the material has properties which render it particularly effective for pacing electrodes, both for stimulating and sensing electrical activity of the heart.

In part, this stems from the two basic mechanisms for current flow across a pacing electrode. One is the purely capacitive mechanism by which electron flow away from the cathode causes electrical charges in the solution at the electrode-electrolyte interface to orient themselves such that a displacement current occurs through the electrolyte. That is to say, because the electrolyte is an ionic medium, the slight displacement of the ions in reorientation creates a charge flow. When the electrical potential across the electrode-electrolyte interface is sufficiently large, chemical reactions begin to occur and current flows. At that point, the mechanism is no longer capacitive, and in the case of heretofore customary electrode materials, the chemical reactions are substantially irreversible.

Although iridium oxide exhibits only fair electrical conductivity compared, say, to titanium—a commonly used electrode material—iridium oxide demonstrates a capacity to readily accept electrons out of an electrolytic solution. From this, I determined that iridium oxide could operate as a highly efficient transducer between an electron flow conductor—in particular, a metal electrode—and an ionic flow conductor—namely, the saline fluid of the body.

Iridium oxide may be deposited as a relatively thick porous layer on a metal substrate for use as a pacing electrode. The porous structure accommodates water from the body saline. In a typical reaction involving a conventional electrode, a negative potential on the electrode repels electrons, and hydrogen is released from the water in the process. In contrast, with an iridium oxide layer relatively tiny potential differences across the electrode-electrolyte interface are effective to produce the reactions and consequent current flow, while the pores trap the reaction products that would otherwise diffuse away and might injure tissue in the vicinity of the stimulation site. More importantly, with the iridium oxide electrode the reactions are reversible upon reversal of the voltage; unlike the situation that exists with conventional pacing electrodes, where reaction products are not recoverable.

A capacitive effect occurs with an iridium oxide coated electrode, but to a considerably lesser extent than that occurring, for example, with a platinum electrode. Rather, the interface across the iridium oxide surface appears to be primarily resistive. Accordingly, an iridium oxide coated pacing electrode exhibits lower polarization than is observed with conventional pacing electrodes; which is to say that the voltage buildup at the interface is smaller for a given charge flow through the iridium oxide electrode, and hence, more energy is available for tissue stimulation.

The reasons for this highly efficient behavior of iridium oxide as such a transducer are not fully understood. It appears to be attributable at least in part to the numerous oxidation states within a film of the material. It is postulated that these oxidation states are relatively stable, with low activation energies, and therefore that the layer tends to perform more as a resistor than a capacitor. The result is that current flow is facilitated, but without the buildup of residual voltages.

In a preferred embodiment of the invention, the iridium oxide layer is confined to the surface of a ring tip pacing electrode adapted to be positioned in electrical contact with heart tissue at a preselected stimulation site. The underlying electrode material may be any metal conventionally utilized for pacing electrode applications, such as titanium, and is preferably but not necessarily a porous structure. The metal substrate is electrically connected to the distal end of the electrically conductive coil within the pacing lead. If desired, a conventional corkscrew may be used in conjunction with the iridium oxide coated ring tip, for active fixation of the electrode at the stimulation site. For bipolar stimulation, the anode, which advantageously may also coated with iridium oxide, is configured as a ring or sleeve flexibly fastened to the cathode but electrically insulated therefrom by a suitable inert material such as silastic. The anode is electrically connected to a second electrically conductive coil within the lead.

In alternative embodiments of the invention, the surface of the underlying electrode metal base or substrate has grooves or recesses in certain regions, and the iridium oxide coating may be confined to the recesses. By controlling the depth of the recesses and the thickness of the iridium oxide layer therein, the major portion of the exposed surface of the iridium oxide layer may be recessed from the outermost surface of the electrode tip. In such a configuration, the current density is greater along the iridium oxide regions, which are slightly removed from direct contact with excitable heart tissue. Therefore, the tissue is less likely to suffer from abrasion or localized pH changes at the electrode-electrolyte interface. Preferably, in these alternative embodiments the electrode tip is a substantially spherical shape, that is more than simply hemispherical, in the case of the stimulating cathode, and the recesses are dimples, circumferential grooves or bands in planes either containing the axis of the sphere or normal to it, or in other relatively regular patterns. In the case of an anodic electrode for bipolar stimulation, the shape may be a ring or sleeve, with recesses or ripples on its surface and an iridium oxide coating. For unipolar stimulation, the anode may be an iridium oxide coated foil or button, bonded to the pulse generator case.

Accordingly, it is a principal object of the present invention to provide an improved pacing electrode with an iridium oxide surface for stimulating or sensing electrical activity of the heart.

Another object of the invention is to provide a pacing electrode having a resistive interface across it to enhance the transfer of electrical energy between it and the cardiac tissue within its immediate vicinity.

Still another object of the invention is to provide a low threshold, cardiac tissue stimulating electrode with a tip portion having an iridium oxide coating thereon to achieve low polarization, with maximum reversibility of surface reactions, and less injury to tissue in the vicinity of the stimulation site.

Yet another object of the present invention is to provide an improved pacing electrode having a surface layer that performs highly efficient transduction between the electron flow in the underlying metallic substrate and the ionic current flow in the electrolyte medium of the body.

BRIEF DESCRIPTION OF THE DRAWINGS

The above and other objects of the invention will become apparent to those of ordinary skill in the field to which the invention pertains, by reference to the accompanying detailed description of the preferred and alternative embodiments taken in conjunction with the drawings in which:

FIGS. 3, 4, 5 and 6 are perspective views of alternative embodiments of a cardiac tissue stimulating cathodic electrode tip portion according to the invention.

FIG. 7 is a perspective view of another embodiment of an anodic electrode according to the invention.

DESCRIPTION OF THE PREFERRED EMBODIMENT

Figure 1:
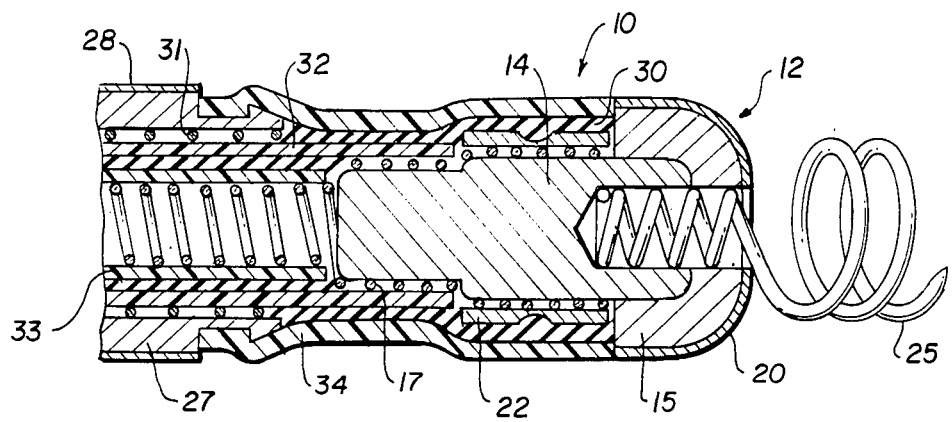
FIG. 1 is a simplified longitudinal cross-sectional view of a cardiac pacing electrode according to the invention, taken along the axis of the configuration, which is circular in transverse cross-section.

Referring now to FIG. 1, a preferred embodiment of a pacing electrode assembly 10 according to the present invention is presented therein. Electrode assembly 10 is part of a spacing lead assembly, as will be described more fully in connection with FIG. 2, and is located at the distal end of the lead assembly relative to the latter's proximal end intended for connection to the pulse generator of a cardiac pacemaker. As much of the basic structure of the electrode assembly is conventional, except as will be pointed out below, the representation in FIG. 1 is intended to be a simplified depiction without need to illustrate known details of electrode structure.

Pacing electrode assembly 10 includes a tip portion 12 and a shank 14. The electrode assembly is configured as an endocardial electrode, in which ring tip 12 is adapted to be positioned in electrically stimulating relationship with excitable cardiac tissue within a selected chamber of the heart. The base or substrate 15 of ring tip 12 is electrically conductive, as is the shank 14, both being composed of any of the conventional metal electrode materials, such as (without limitation) platinum, platinum-iridium alloy, iridium, tantalum, or titanium. Preferably, both shank 14 and tip substrate 15 are composed of titanium. Shank 15 is cylindrical, with a diameter of about 0.06 inch at its widest portion. The shank is press-fitted into the mating receptacle of U-shaped tubular ring tip 12, such that the two portions are virtually integral mechanically, and in firm electrical contact. A coil 17 of electrically conductive wire at the distal end of the lead (which at its proximal end is adapted for connection to a source of electrical stimulation pulses) is closely contained about and in good electrical contact with shank 12, and thus with ring tip 12.

According to the invention, the surface of the electrode tip 12 intended and adapted to be positioned in stimulative relationship with excitable myocardial tissue is coated with a film or layer 20 of iridium oxide. Surface layer 20 may be an AIROF, SIROF, TIROF (thermal iridium oxide film), or a coating applied in any other suitable manner, and preferably has a thickness on the order of 200 nanometers, although any layer thickness exceeding about 100 nanometers appears to be satisfactory to obtain the desirable results. The iridium oxide layer 20 on substrate 15 has an exposed surface area of approximately 8.5 square millimeters. Preferably, tip substrate 15 has a porous surface structure. Although the invention is not so limited and may be utilized with substantially non-porous substrates as well, a porous substrate surface is desirable because the iridium oxide coating will follow the lacework contour and a porous surface is useful to promote cardiac tissue ingrowth and thereby to reduce abrasion.

The substrate 15 may be formed using a conventional process of powder metal metallury, in which titanium powder is packed into a mold, compressed, and thereafter sintered at a temperature and for a time sufficient to cause partial melting of the compressed powder into a relatively porous electrically conductive structure.

The substrate may be reactively coated with iridium oxide in a conventional diode RF sputtering system. First, the substrate is positioned and maintained in good thermal contact with the water cooled platform of the sputtering system. Any portion of the surface which is not to be coated is suitably masked. Pre-sputtering is performed with an iridium target in pure oxygen at an ambient pressure of about 20 microns for approximately 20 minutes to one-half hour. The pressure is then reduced to the range from aoubt 2 to 4 microns, and sputtering is performed with a target power density of about 0.6 to 0.8 watt per square centimeter. The process is continued until an iridium oxide layer of the desired thickness is deposited, about three hours for a 200 nanometer thickness. The resulting IrO layer is a SIROF.

A tubular metal sleeve 22 encircles a portion of coil 17 and is crimped to assure good electrical contact between the electrode tip 12 and the coil, via shank 14. A central mating hole and bore in tip 12 and shank 14 are utilized to receive and fixedly retain a conventional corkscrew 25 if it is desired to provide active fixation of the electrode assembly 10 in the myocardium.

A second electrode (anode 27) in the form of a cylindrical sleeve of titanium or other conventional metal electrode material is insulatively spaced sufficiently behind ring tip 12 to avoid the shunting of substantial current between the edges of the two electrodes. Anode 27 may be coated with a layer 28 of iridium oxide at its exposed surface, in the same manner as cathodic electrode tip 12. A second coil of electrically conductive wire 31 is maintained in good electrical contact with the interior of another 27. This may be accomplished, for example, by containing coil 31 between the anode and a metal ring (not shown) at the far end of the anode, and employing a crimp joint on the ring. Coil 31 forms part of the pacemaker lead, and is adapted at its proximal end (not shown) for connecting the anode to a source of reference potential at the pulse generator. An electrically insulating mass 30 of silicone rubber may be used to encapsulate the internal elements of the electrode assembly, including the wire coils, the shank 14, metal sleeve 22, and polyurethane sleeves 32 and 33. An outer polyurethane sleeve 34 extends between electrode tip 12 and anode 27.

Figure 2:
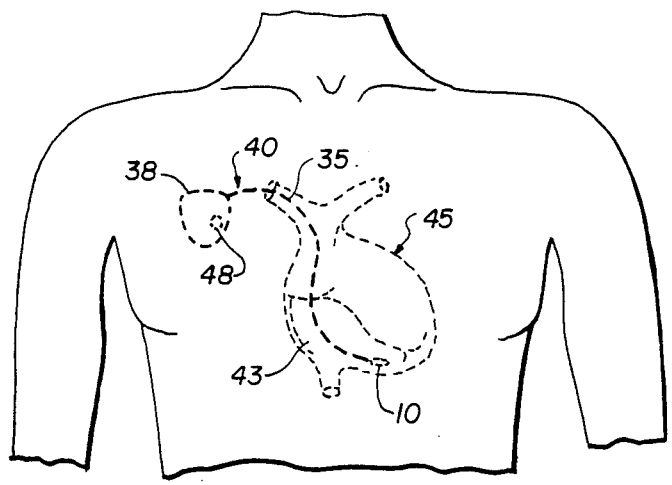
FIG. 2 is a simplified pictoral representation depicting an alternative embodiment of a pacing electrode in a lead assembly arranged for unipolar stimulation, as part of a cardiac pacemaker implanted in the body.

Referring now to FIG. 2, a pacing lead assembly 35 includes electrode assembly 10 at its distal end and is connected at its proximal end to appropriate points of electrical potential of the conventional circuitry, including the pulse generator, housed within a metallic case 38. The combination of the circuitry in case 38 and the pacing lead assembly 35 constitutes cardiac pacemaker 40. As shown in FIG. 2, the pacing lead assembly 35 is inserted pervenously until the iridium oxide coated ring tip of the electrode assembly 10 is properly positioned in contact with or adjacent to stimulatable heart tissue within the selected chamber; in this example, the right ventricle 43 of the patient's heart 45. The pulse generator (as the batteries, generator and other electronic circuitry housed within case 38 are often collectively called) includes an electrical connector (not shown) for mating with the proximal end of the pacing lead assembly. The case is implanted in a subcutaneous pouch in the patient's chest, after the connections are made to the lead assembly. In operation, electrical stimuli from the pulse generator are impressed on the stimulating electrode at a rate within the range selected to provide the desired pacing.

The pacing lead assembly may be arranged for unipolar stimulation by conventional assembly without an integral anodic electrode, with the case 38 or portion thereof used as the anode. According to another aspect of the invention for use in unipolar stimulation, the anode comprises a limited region 48 of iridium oxide film. Region 48 may be an iridium foil substrate which has been anodized to form an AIROF film thereon, and the uncoated side of the foil then conductively bonded to titanium case 38. Alternatively, region 48 may comprise a titanium or iridium button on which a SIROF iridium oxide layer has been sputtered in the manner described earlier herein. As with the previously described embodiment, a layer thickness in a range exceeding 100 nanometers is preferred.

In an exemplary preparation of an AIROF electrode, the iridium foil is cleaned and polished ultrasonically in an ethanol bath, followed by etching of the foil surface by immersion in mild saline solution and applying a sinusoidal voltage of 15 volts at 10 Hz between the foil and a reference electrode (such as platinum) for a period of about 60 seconds. An iridium oxide layer is then grown on the etched iridium foil by cyclic anodization of the foil at room temperature in an electrolyte consisting of a mild solution of sulfuric acid. The anodization is carried out by application of a triangular voltage between the foil and the electrolyte, of between +0.24 V and −1.25 V as measured with a calomel electrode, for a period of time sufficient to produce an iridium oxide layer of the desired thickness. One side of the foil is then cleaned and bonded to case 38, such as by welding, to form a good electrical connection therebetween.

Altneratively, the iridium foil (or other iridium layer) may be oxidized to form the iridium oxide coating by repeatedly oven-heating it to about 800° C. after wetting the surface with a mild caustic hydroxide solution. The resulting TIROF may be cleaned by boiling in water and rinsing.

Referring now to FIG. 3, an alternative embodiment of a stimulating cathode 50 comprises a spherical tip 51 fastened to a tubular shank 53, each of which is composed of solid titanium. Tip 51 has a plurality of recesses formed in a regular pattern of dimples 56 on its outer surface. In practice, tip 51 and shank 53 may be formed as one integral piece in a single mold, using a conventional technique such as powder metal metallurgy. The dimples may be formed in the tip by providing suitably rounded bumps on the surface of the mold. According to this embodiment of the invention, the iridium oxide layer 60 may be confined to the dimples. This may be accomplished, for example, by using any of the iridium oxide coating techniques described earlier herein to form an iridium oxide layer over substantially the entire surface of spherical tip 51, and then polishing the surface to remove the layer except within the dimples.

Another embodiment of a stimulating pacing cathode according to the invention is shown in FIG. 4. The electrode 65 includes spherical tip 67 and cylindrical shank 69 fabricated in the manner described above. However, in this embodiment the tip has a plurality of spaced circumferential ribs 70 lying at its surface and defining therebetween a plurality of recessed regions 73. In this embodiment, the iridium oxide coating 75 is formed over the entire surface of tip 67. If desired, the tip 67 may thereafter be polished to remove the IrO from the ribs and to confine it to the surface of each recessed region 73. Although the ribs are shown in FIG. 4 as lying at the intersections of the spherical surface and planes containing the longitudinal axis of the tip-shank configuration, the ribs may instead be formed to lie in circumferential bands or rings perpendicular to the longitudinal axis.

In yet another alternative embodiment of a pacing electrode, shown in FIG. 5, the spherical tip 80 is conductively fastened to shank 81 and has a regular pattern of ribs 83 forming the sides of polygons along its surface. The polygonal regions are recessed relative to ribs 83. Iridium oxide layer 85 overlies the surface at tip 80, and may be formed thereon by any of the known methods of providing an iridium oxide layer on a metal substrate, whether as a TIROF, SIROF or AIROF. If desired, this may be followed by polishing the oxide coating from the raised ribs 83 to confine it to the recesses. If such confinement is desired, the depth of the recesses may be such that the surface of the iridium oxide coating thereon is itself recessed relative to the polished surfaces from which the iridium oxide layer has been removed.

Each of the spherical tip-on-stem configurations of FIGS. 3, 4 and 5 may be manufactured as previously described herein. A conductive wire coil (not shown in these FIGS.) may be maintained in good electrical contact with the conductive stem (shank) either at its internal surface along the axial hole, or about its external surface, by a crimped metal sleeve in the manner of FIG. 1. The conductive coil may then be encapsulated in silicone rubber or any other material commonly employed for such purpose, except at the points of contact with the stem.

The anodic electrode use in conjunction with any of these spherical stimulating cathode tips may be of the bipolar ring type (such as electrode 27 of FIG. 1 for bipolar stimulation) or may be the metallic case or a portion thereof or a layer or button attached thereto (such as electrode 48 of FIG. 2 for unipolar stimulation).

Referring now to FIG. 6, yet another embodiments of a stimulating cathodic electrode according to the invention comprises a tip portion 86 having a base or substrate 87 and an iridium oxide layer 88 overlying the substrate. In this embodiment, the electrode substrate is of generally hemispherical shape with grooves 89 cut in spaced concentric rings each sharing the longitudinal axis of the tip portion. Here again, the substrate may be composed of any material conventionally utilized for a pacer stimulating electrode, and iridium oxide layer 88 may be an AIROF, SIROF or TIROF. As previously mentioned, the IrO coating will generally follow the contours of the substrate surface, including the intricate lacework of a porous surface.

The grooves in tip portion 86 will provide regions of high current flux density, when the electrode is utilized in operation of the cardiac pacemaker. As with the other embodiments described herein, the iridium oxide layer may be confined to the surface of the recesses (grooves 89) only, rather than covering the entire surface of the tip portion as shown in FIG. 6.

Referring now to FIG. 7, another embodiment of an anodic electrode for bipolar stimulation comprises ring anode 90. According to this aspect of the invention, anode 90 has a tubular configuration with a rippled or wavy outer surface 92. This configuration may also be produced using powdered titanium which is compacted in a suitable mold, followed by sintering. Iridium oxide layer 95 is formed on the wavy outer surface using one of the techniques discussed above. This shape tends to assure retention of the iridium oxide in the narrowed or "necked" surface regions 97. The thickness of layer 95 is preferably about 200 nanometers.

Referring again to FIG. 2, electrode assembly 10 may include any of the spherical tip-on-stem cathodes 50, 65 or 80 or hemispherical tip 86 of FIGS. 3, 4, 5 or 6, respectively, rather than the ring tip cathode 12 of FIG. 1. Rather than the active fixation of the stimulating cathode tip in the endocardium provided by corkscrew 25, in the embodiment of FIG. 1, passive fixation elements such as flexible tines may alternatively be employed at the distal end of the lead near the electrode assembly. With a porous tip ingrowth of fibrous tissue over time will further assist to maintain the electrode in position. As is customary with implantable cardiac pacemakers, all exposed portions of the pulse generator case 38 and pacing lead assembly 35 are rendered inert to body fluids. In typical practice, the pacing lead assembly is manufactured and distributed as an article of commerce separate from the pulse generator unit, but the invention is not restricted to such practice, and may be utilized in pacemakers having a lead assembly integral with the pulse generator case. As previously noted, electrode assembly 10 may be configured for bipolar stimulation, with an anode such as 27 in the embodiment of FIG. 1, or for unipolar stimulation, with an anode such as 48 on case 38 in the arrangement of FIG. 2.

The efficient transduction of the iridium oxide layer on the cathode tip results in a low threshold of stimulation of excitable heart tissue in the vicinity of the stimulation site, under the influence of the electric field. Acute stimulation thresholds as low as approximately 0.2 volt have been observed in dog tests using a ring tip stimulating cathode of the type described with reference to FIG. 1. Where the iridium oxide layer is confined to recessed regions on the cathode tip, the virtual electrode surface is somewhat closer to the actual surface of the spherical tip. The site of greater current flow at the recessed iridium oxide regions tends to reduce irritation of and injury to stimulatable tissue.

Other embodiments of the invention will become apparent to those of ordinary skill in the field to which it pertains from a reading of the foregoing description in conjunction with the accompaying drawings. Accordingly, the invention is to be limited only as defined by the appended claims.

I claim:

1. A cardiac pacing lead assembly, comprising
   an electrode means having a tip portion provided with an exposed surface layer of iridium oxide situated to be in electrically coupled relationship with excitable cardiac tissue of the heart when said lead assembly is implanted in a human patient, for alternatively stimulating said cardiac tissue when said electrode means is electrically energized and sensing electrical activity of the heart in response to said stimulation when said electrode means is de-energized, and
   an electrical conductor means electrically connected at one end thereof to said tip portion for delivering electrical energization thereto and for conducting signals representing said electrical activity therefrom, and having terminal means at the other end for connection to a pulse generator of a cardiac pacemaker.

2. The pacing lead assembly of claim 1, in which the surface of the tip portion is porous and said iridium oxide surface layer follows the interstices of said porous surface.

3. The pacing lead assembly of claim 1, in which said surface layer of iridium oxide has a thickness exceeding 100 nanometers.

4. The pacing lead assembly of claim 1, further including
   a second electrode means having an iridium oxide surface layer and insulatively spaced from the first-mentioned electrode means in fixed relationship therewith, for cooperation with said first-mentioned electrode means to provide bipolar stimulation of the patient's heart, and
   a second electrical conductor means electrically connected at one end to said second electrode means and having further terminal means at the other end thereof for connection to a point of reference potential of said pulse generator.

5. An implantable lead assembly for electrical conduction between an electrical energy processing means and the endocardium of a human heart, said lead assembly comprising
   an electrode means having a size and shape configured to be insertable into a selected chamber of the heart and positioned in proximity to the endocardium for impressing electrical stimuli thereon and for sensing electrical signals indicative of the behavior of said heart in response thereto,
   an electrical conductor means, having a proximal end with terminal means for electrical connection to said energy processing means and having a distal end electrically connected to said electrode means, for alternately conducting said electrical stimuli and said sensed electrical signals therebetween.
   said electrode means including an electrically conductive tip comprising a substrate and an exposed surface layer of iridium oxide overlying and integral with said substrate.

6. The lead assembly of claim 5, wherein
   the surface of said substrate is dimpled and porous, and said surface layer of iridium oxide resides within the interstices of the pores in the dimples.

7. The lead assembly of claim 5, wherein
   said iridium oxide surface layer has a thickness of at least 100 nanometers.

8. A cardiac pacemaker for stimulating and sensing electrical activity of a human heart, comprising
   a pulse generator means,
   means for supplying electrical power to said pulse generator means,
   an electrode means having a tip portion provided with a surface layer of iridium oxide to electrically interact with excitable cardiac tissue of said heart for impressing an electric field on said cardiac tissue when electrically energized and for sensing electrical activity of the heart in response to said impressed field when de-energized, and
   a conductor means having a distal end and a proximal end, said distal end electrically connected to said electrode means and said proximal end electrically connected to said pulse generator means, for conducting electrical energy between said generator means and said electrode means.

9. The cardiac pacemaker of claim 8, in which said iridium oxide layer has a thickness of at least 100 nanometers.

10. A method of artificially pacing a heart, comprising the steps of
    introducing an implantable lead, having at its distal end an electrode coated with an iridium oxide layer, intravenously into a selected chamber of a patient's heart, so that said electrode is positioned with said iridium oxide layer in cardiac tissue stimulating relationship with the endocardium of said heart,
    impressing electrical stimuli on said electrode at a rate within the range selected to provide the desired stimulation of the heart, and
    sensing the electrical activity of the heart detected at the surface of said iridium oxide layer to determine whether the heart is properly responding to said stimuli.

11. The method of claim 10, in which the introduction of said electrode is pervenously into a selected chamber of the heart for stimulation via the endocardium.

* * * * *

UNITED STATES PATENT AND TRADEMARK OFFICE
CERTIFICATE OF CORRECTION

PATENT NO. : 4,679,572

DATED : July 14, 1987

INVENTOR(S) : Ross G. Baker, Jr.

It is certified that error appears in the above-identified patent and that said Letters Patent is hereby corrected as shown below: Title page:

In the Abstract, 4th line, delete "of" (first occurrence) and insert --or--.

Below the Abstract, delete "11" and insert --10--.

Col. 1, line 18, delete "propagated the" and insert --propagated through the--.

Col. 3, line 27, delete "behavoir" and insert --behavior--.

Col. 6, line 59, delete "spacing" and insert --pacing--.

Col. 7, line 12, delete "15" and insert --14--;
line 21, delete "12" and insert --14--;
line 56, delete "aoubt" and insert --about--.

Col. 8, line 11, delete "containing" and insert --confining--.

Col. 10, line 9, delete "use" and insert --used--.

Col. 11, line 32 (Claim 1), delete "alternatively" and insert --alternately--.

Col. 12, delete lines 63-66 (Claim 11).

Signed and Sealed this

Twelfth Day of January, 1988

Attest:

DONALD J. QUIGG

Attesting Officer

Commissioner of Patents and Trademarks